Figure 1:
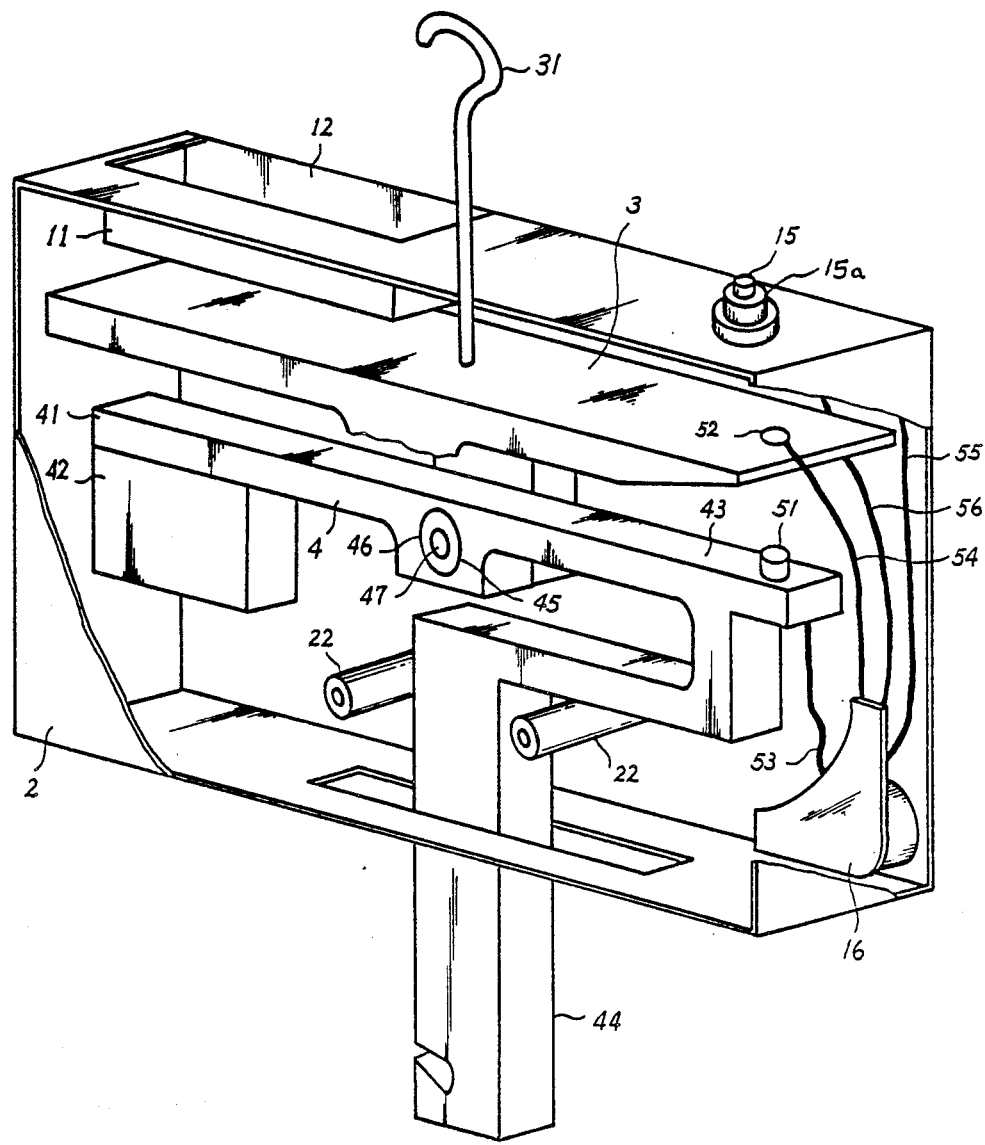

United States Patent [19]

Chiang

[11] Patent Number: 4,931,777
[45] Date of Patent: Jun. 5, 1990

[54] LOW LEVEL ALARM FOR DROP-FEED INJECTION LIQUID

[76] Inventor: Cheng-San Chiang, No. 32, Chung-San Road, Tau-Yang, Taiwan

[21] Appl. No.: 271,703

[22] Filed: Nov. 16, 1988

[51] Int. Cl.[5] ............... G08B 21/00; G01F 23/18
[52] U.S. Cl. .................. 340/613; 128/DIG. 13; 177/46; 340/625
[58] Field of Search ............... 340/625, 613; 177/46, 177/190, 246; 128/DIG. 13; 73/296

[56] References Cited

U.S. PATENT DOCUMENTS

| | | | |
|---|---|---|---|
| 2,706,755 | 4/1955 | Krasno | 340/613 X |
| 3,287,721 | 11/1966 | Baehr | 340/613 |
| 3,389,387 | 6/1968 | Hulse et al. | 340/613 |
| 3,425,415 | 2/1969 | Gordon et al. | 340/613 X |
| 3,934,474 | 1/1976 | Whitinger | 73/296 |
| 3,977,567 | 8/1976 | Rudd | 128/DIG. 13 X |
| 4,137,915 | 2/1979 | Kamen | 340/613 X |
| 4,176,349 | 11/1979 | Fliegel | 340/613 |
| 4,198,626 | 4/1980 | Rauscher | 340/613 |
| 4,670,007 | 6/1987 | Wheeldon et al. | 128/DIG. 13 X |

FOREIGN PATENT DOCUMENTS 1288411 2/1962 France ............ 128/DIG. 13

Primary Examiner—Tom Noland
Assistant Examiner—Joseph W. Roskos
Attorney, Agent, or Firm—Larson & Taylor

[57] ABSTRACT

A low level alarm device for drop-feed injection liquid comprises a mechanical arrangement where an injection liquid containing bottle is hung on one arm of a mechanical balance to be balanced by a counter weight provided on the other arm of the balance. The consumption of the liquid in the bottle causes the loss of equilibrium of the balance thereby triggering a circuit to be closed to sound an alarm so that the liquid may be replenished in time by an attendant.

6 Claims, 2 Drawing Sheets

LOW LEVEL ALARM FOR DROP-FEED INJECTION LIQUID

The present invention relates to a low level alarm devised for clinical use and more particularly to a low level alarm for drop-feed injection liquid contained in a bottle when the liquid is being consumed for such as intravenous injection for a patient.

The low level of an intravenous injection liquid should always be monitored so that it can be replenished in time otherwise the exhaustion of the liquid would draw air bubbles into the blood stream which means a matter of life and death. Doctor, nurse or even the family of the patient who is receiving the injection is often obliged to take such a watching job, yet negligence occurred from time to time which could be a result of the stress built-up of those attendants, sometimes even within the patient himself.

A device for monitoring the level of the injection liquid is not unknown. One such device includes a part to be immersed into the liquid. However, the nature of the material to be immersed may constitute a contamination to the liquid. The practice is most undesirable because the introducing of any foreign matter into the liquid which is supposed to be pure and bacteria free could jeopardize seriously the life of the patient in concern.

Another prior art device utilizes a spring balance where the level of the injection liquid is expressed in the term of weight measure. The consumption of the liquid is reflected in the retraction of the spring which may trigger a certain alarm. The device seems simple yet it is not sensitive enough and the fatigue of the spring may fail to perform a job satisfactorily.

On the other hand, devices which take advantage of an electronic balance may serve for the purpose and have the above said drawbacks eliminated, however, the device would be complicate to some extent and higly expensive.

Therefore the main object of the present invention is to provide a low level alarm built according to the principle of a dual armed balance, to which one of the arms of the balance beam is provided with a dead counter weight that fixed the moment of the said arm about the fulcrum of the balance beam. On the other arm of said balance, a bottle of injection liquid to be consumed is suspended, the lowering of the liquid level causes the off-balance of the beam constituting the dual arms. Trigger means is provided on the one arm where the liquid bottle is hung. When the beam dips to an preset alarming degree, (say, indicating only 30 to 50 cc of liquid left) a circuit is closed to sound an alarm.

Figure 2:
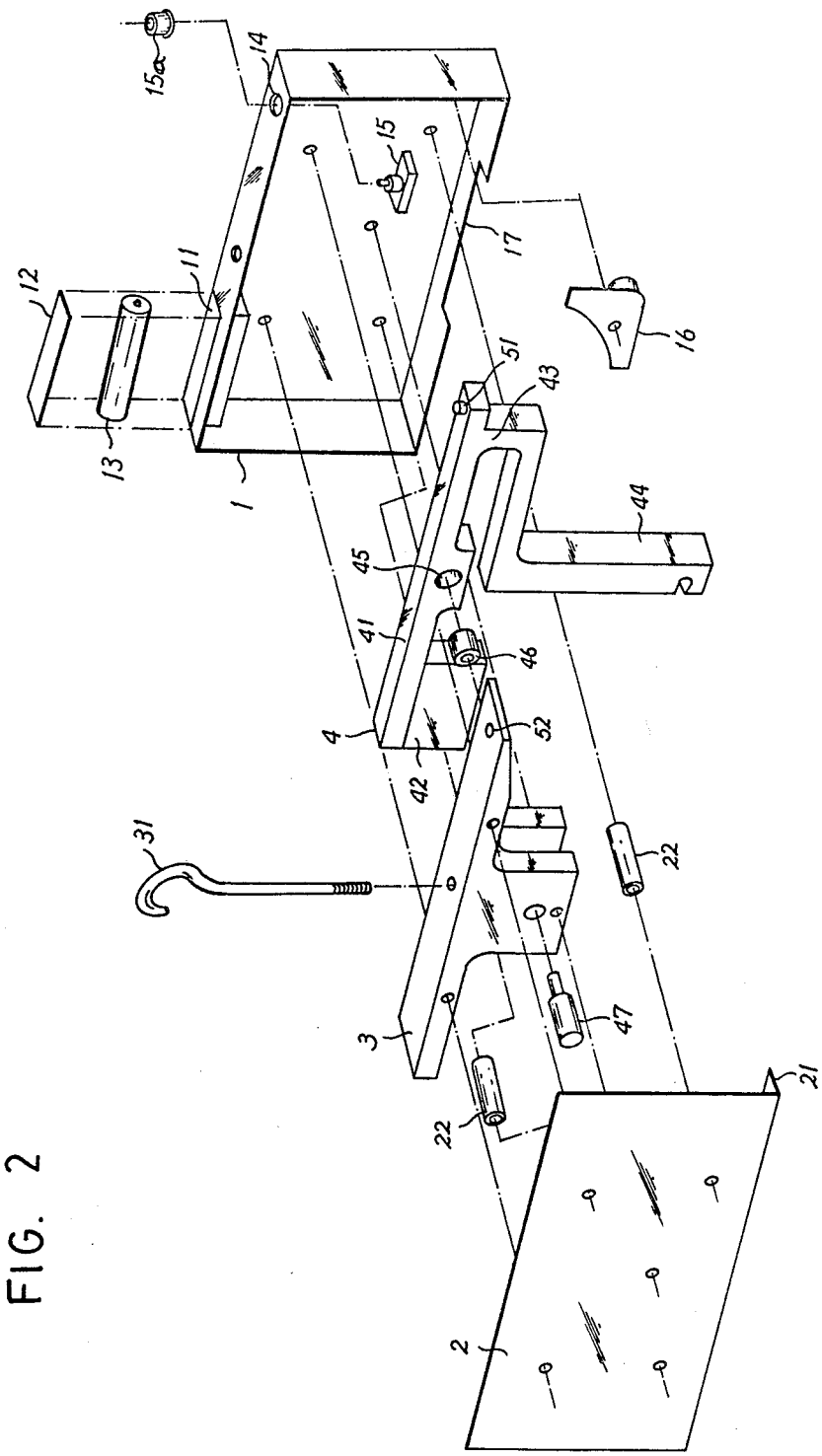

Other object and features of the present invention may become apparent with the following detailed description taken in conjunction with the annexed drawings:

FIG. 1 is a perspective view of an embodiment of the low level alarm for drop-feed injection liquid of the present invention with partial cut-away of the housing and the cover thereof; and FIG. 2 is an exploded view in perspective of the same embodiment shown in FIG. 1.

Now referring to FIG. 1 and FIG. 2, the low level alarm for drop-feed injection liquid comprises a rectangular shaped housing 1 and a cover 2 incorporated to hold the main mechanism of the device.

In the left upper corner of the housing 1, a recessed chamber 11 is provided for the retaining of a dry cell 13 which is the power source of the alarm. On a top opening of the chamber 1 there is a clip-on lid of conventional type. At the right corner of the upper side wall of the housing 1, an opening 14 is provided for the disposition of a reset button 15 of known type with a lock nut 15a to be screwed thereon for fixing. A cut out 17 is formed on the lower side wall of the housing 1 to accomodate the possible swing of a downwardly extended suspender 44 which is to be related later. A cover 2 is attached to a pair of spacing posts 22—22 pre-screwed on the rearwall of the housing 1. Cover 2 has a rearward protruded lip 21 thereundeer to hold its upright position.

A retaining bracket 3 generally of T shape with a bifurcated downwardly depending base having two spaced apart legs is fixedly mounted between rear wall of the housing 1 and the cover 2 through conventional means such as machine screws which are not numbered. Underneath and in between the legs of the bracket 3, a beam 4 of a dual-arm mechanical balance is pivotally mounted on a pivot shaft 47 that extends through a bushing 46 borne in a central aperture 45 in beam 4.

The left arm 41 (as depicted in FIG. 2) of the beam 4 having a counter weight 42 attached thereunder is in swingable balance rotating about the pivot shaft 47 with the right arm 43 which extends downwardly after finishing a horizontal U turn. The overall configuration of the beam 4 is generally like an earmark. The downwardly extended stem of the right arm 43 of the beam 4 comprises a suspender 44 for the hanging of a bottle injection liquid (not shown) thereunder.

The center of gravity of the summation weight W2, a resultant of the weight of the right arm 43 plus the weight of liquid bottle suspended thereunder, lies quite a short distance, say D2 from the pivot center 47. When a mechanical balance is in a balance state, the right side moment W2D2 must equal to the left side moment W1D1, where W1 is the summation of the weight of the left arm 41 and that of the counter weight 42, and D1 is the distance between center of gravity of W1 and the pivot center 47. The relationship W1D1=W2D2 holds true until the consumption of the liquid in the bottle causes off-balance.

A first electrical contact 51 disposed on the right top of arm 43 tends to rise facing a second contact 52 disposed under the bracket 3 at a position corresponding to contact 51. When the off-balance reaches a certain extent, beam 4 has pivoted or rotated to such a degree that the two electrical contacts meet to close a circuit to sound an alarm telling that the replenishment of the injection fluid is urgently needed. The alarm noise is created through a buzzer means 16 located in the lower right corner within the housing 1. Connection wires respectively of the first contact 51 to buzzer 16 and buzzer 16 to the second contact 52 are shown in the FIG. 1 as 53 and 54, the connections from/to the dry cell being omitted for clarity.

Another pair of wires 55, 56 lead from the push button 15 (FIG. 1) which is connected in series in the alarm circuit to serve for the purpose of breaking deenergizing the alarm when the attendant has noticed the low level and the replenishment is being taken care of. After the liquid bottle has been refilled, the attendant should push once more the button to set it back to a normal closed state as it was.

The contacts 51–52 are disengaged when the liquid supply is restored, the alarm silences until another low level shows up.

A swivel hook 31 is screwed into a threaded hole on top of the bracket 3, through an opening in the top wall of housing 1, to facilitate the hanging up of the whole device on a stand commonly used in the clinics. Thus being, the suspender 44 is free for use. The device of the present invention does not involve any complicated techniques, such as electronics, with the simple structure based upon a sound principle and background, yet sophisticated enough to give reliable effect.

The above said illustration is made through preferred embodiment which is by way of exemplification but not limitation, variation in application can be easily adapted such as a plastic bottle may be used which is some 300 gm lighter than a glass bottle, in case the device is first set according to a glass bottle, a small weight corresponding the difference may be added to the suspender when a plastic bottle is used instead.

Those who skilled in the art may modify the device without depart from the spirit and scope of the invention which is set forth in the annexed claims.

What I claimed is:

1. A low level alarm for drop-feed injection liquid comprising:
    a housing to hold the following mechanism of the device, including:
    a chamber for holding a battery as a power source;
    an electrical alarm means connected to said electrical source for giving an audible signal upon a low level condition;
    trigger means for the alarm means to be actuated at low level of the liquid;
    a switch means for deenergizing the alarm when the liquid has been replenished; and
    a mechanical balance means comprised of a balance beam having two extended arms with one arm provided with suspender means to take a conventional drop-feed injection liquid bottle while the other arm includes a counter weight for balance; wherein the balance is an equilibrium state when the bottle is full of liquid and the consumption of the liquid causes a pivoting of said beam which ultimately triggers the alarm when the preset low level has been reached.

2. The low level alarm according to claim 1, wherein the balance beam has two extended arms and is pivotally supported in a mounting bracket fixedly mounted within said housing, and said one arm having suspender means is made to turn downwardly to facilitate the hanging of the liquid bottle thereunder.

3. The low level alarm according to claim 1, wherein said trigger means is comprised of two electrical contacts, one of said contacts is disposed on the top corner of said one arm having suspender means to take the liquid bottle and the other of said contacts disposed at a corresponding position under said mounting bracket, so that when the low level is reached, the pivoting of said balance beam has lifted the arm suspending the bottle, thereby engaging said two contacts to close the alarm circuit.

4. The low level alarm according to claim 1, wherein said alarm means, said trigger means and said switch means are connected in a series circuit to said power source to complete the alarm circuit, and wherein said switch means is set up in a normal closed state, such that when the liquid is being replenished, said switch means can be manually pushed "off" to open the circuit to deactivate the alarm and when the replenishment is complete said switch means can be reset into its original normal closed state.

5. The low level alarm according to claim 1, wherein the said switch means is manually operated and is comprised of a push button switch, and wherein the alarm device is a buzzer.

6. The low level alarm according to claim 1 wherein said housing is of generally rectangular shape with a cover.

* * * * *